(12) United States Patent
Boyer et al.

(10) Patent No.: US 7,899,827 B2
(45) Date of Patent: Mar. 1, 2011

(54) SYSTEM AND METHOD FOR THE INDEXING OF ORGANIC CHEMICAL STRUCTURES MINED FROM TEXT DOCUMENTS

(75) Inventors: Stephen Boyer, San Jose, CA (US);
Anna Rosa Coden, Riverdale, NY (US);
James William Cooper, Wilton, CT (US)

(73) Assignee: International Business Machines Corporation, Armonk, NY (US)

( * ) Notice: Subject to any disclaimer, the term of this patent is extended or adjusted under 35 U.S.C. 154(b) by 645 days.

(21) Appl. No.: 10/797,359

(22) Filed: Mar. 9, 2004

(65) Prior Publication Data

US 2005/0203898 A1    Sep. 15, 2005

(51) Int. Cl.
*G06F 17/30* (2006.01)

(52) U.S. Cl. .............................. 707/741; 704/7; 704/9; 704/10; 706/47; 706/55

(58) Field of Classification Search ....................... None
See application file for complete search history.

(56) References Cited

U.S. PATENT DOCUMENTS

| | | | | |
|---|---|---|---|---|
| 5,577,239 | A * | 11/1996 | Moore et al. | 707/3 |
| 6,182,029 | B1 * | 1/2001 | Friedman | 704/9 |
| 6,304,869 | B1 | 10/2001 | Moore et al. | 707/3 |
| 7,054,754 | B1 * | 5/2006 | Brecher | 702/19 |
| 2002/0087508 | A1 * | 7/2002 | Hull et al. | 707/1 |

OTHER PUBLICATIONS

Garfield, An Algorithm for translating chemical names to molecular formulas, Doctoral Dissertation, (originally published 1961, Library of Congress Catalog Card No. 61-17455, Institute for Scientific Information), republished in essays of an information scientist, vol. 7, p. 441-513, 1984, Institute for Scientific information.*

Kemp et al., J. Chem. Inf. Comput. Sci., vol. 38, p. 544-551, 1998.*
Dittmar et al., J. Chem. Inf. Comput. Sci., vol. 23, No. 3, 93-102,1983.*
Leiter et al., J. Chem. Doc., vol. 5, N. 4, p. 238-242, 1965.*
Drefahl et al., J. Chem. Inf. Comput. Sci., vol. 33, 886-895,1993.*
Shivaratri et al., Computer, p. 33-44, Dec. 1992.*
Allen et al. (Journal of Chemical Information and Computer Sciences, vol. 17, No. 1, p. 9-15, 1977).*
Singh et al.( J. Chem. Inf. Comput. Sci. 2003, 43, 743-752).*
Cardinali (Industrial Management + Data Systems. Wembley: 1994. vol. 94, Iss. 4; p. 3, 6 pgs).*
Vander Stouw (Journal of Chemical Documentation, vol. 14, No. 4, p. 185-193, 1974).*
"Smiles Parser", http://www.wag.caltech.edu/home/meulbroek/smiles/smiles_parser.htm, Feb. 24, 2004, 2 pgs.
"SMILES Specification", http://umbbd.ahc.umn.edu/core/SMILES.html, Feb. 24, 2004, 1 pg.
Narayanaswamy et al., "A Biological Named Entity Recognizer", 12 pgs., 2003, Pac Symp Biocomput. 2003:427-38.
Wilbur et al., "Analysis of Biomedical Text for Chemical Names: A Comparison of Three Methods", 5 pgs., 1999, Proc AMIA Symp. 1999: 176-180.

* cited by examiner

*Primary Examiner*—Karlheinz R Skowronek
(74) *Attorney, Agent, or Firm*—Harrington & Smith (57) ABSTRACT

Disclosed is a method, a computer program product and a system for processing documents that contain chemical names. The system has a unit to partition document text and to assign semantic meaning to words; a unit to recognize any substructures present in the chemical name fragments; and a unit to determine structural connectivity information of the chemical name fragments and recognized substructures and to store the determined structural connectivity information in a searchable index. The system further includes a unit to search a text index using at least one of a fragment name and a substructure name and to search the structure index by at least one of fragment connectivity and substructure connectivity. At an intersection of the search results from the structure index and the text index, the system operates to identify at least one document that contains a reference to a corresponding chemical compound.

26 Claims, 5 Drawing Sheets

| Cℓ | CH₃ | ⬡ | ⬡⬡ | N=N | C=O |
|---|---|---|---|---|---|
| chloro | methyl | phenyl | benzo | diazepin | one |

SYSTEM AND METHOD FOR THE INDEXING OF ORGANIC CHEMICAL STRUCTURES MINED FROM TEXT DOCUMENTS

CROSS-REFERENCE TO A RELATED PATENT APPLICATION

This patent application is related to copending and commonly assigned U.S. patent application Ser. No. 10/670,675, filed Sep. 24, 2003, entitled: "System and Method for the Recognition of Organic Chemical Names in Text Documents", by Anna R. Coden and James W. Cooper, the content of which is incorporated by reference herein in its entirety.

TECHNICAL FIELD

This invention relates in general to digital libraries and life science documents and, more specifically, it relates to apparatus and methods for searching and analyzing scientific documents, such as journal publications and patents, for the occurrence of names of organic chemicals and for indexing their chemical structures.

BACKGROUND

Regardless of the technology being used, most system for the analysis and indexing of documents for search and information retrieval follow the same basic procedure. First the data are separated into individual documents and each document is divided into text tokens. These tokens are then combined into meaningful phrases and fragments that are indexed for retrieval. An index contains data that is used for search and document analysis to process queries and identify relevant objects.

After the index is constructed, queries may be submitted to the search system. The query represents information that is desired by the user, and is expressed using a query language and syntax defined by the search system. The search system processes the query using the index data for the database and a suitable similarity ranking algorithm. From this, the system returns a list of topically relevant objects, often referred to as a "hit-list". The user may then select relevant objects from the hit-list for viewing and processing.

In a network environment, the components of a text search system may be distributed across multiple computers. A network environment contains two or more computers connected by a local or a wide area network, (e.g., Ethernet, Token Ring, the telephone network, and the Internet). A user accesses a hypermedia object database using a client application on the user's computer. The client application communicates with a search server (e.g., a hypermedia object database search system) on either the computer (e.g., the client) or another computer (e.g., one or more servers) on the network. To process queries, the search server needs to access just the database index, which may be located on the same computer as the search server or on another computer on the network. The actual objects in the database may be located on any computer on the network.

A Web environment, such as the World Wide Web on the Internet, is a network environment where Web servers and browsers are used. Having gathered and indexed all of the documents available in the collection, the index can then be used, as described above, to search for documents in the collection. Again, the index may be located independently of the objects, the client, and even the search server. A hit-list, generated as the result of searching the index, will typically identify the locations and titles of the relevant documents in the collection, and the user then retrieves those documents directly using the user's Web browser.

Text mining of documents can also be performed as part of document indexing. Text mining involves the recognition of document parts, such as paragraphs and sentences, and then the analysis of each recognized document part (e.g., each sentence). Sentence analysis involves the tagging of each word with its part of speech and then the parsing of each sentence into its component parts. The result of sentence parsing is a parse tree of the parts and sub-parts of that sentence. This information is typically stored in tables for retrieval. Frequently these tables are database tables with database indexes associated with them.

Such parsing and data storage can then be used to deduce the overall meaning of the document and the relations between parts of the document.

The ability to search patent and patent-related literature for information related to chemical entities is particularly challenging. The nomenclature associated with chemical substances is difficult to understand, and often inconsistent chemical terms are used to express the same or similar chemical entities. Despite attempts to standardize the chemical nomenclature by international standards committees such as the Union of Pure and Applied Chemist (IUPAC), these rules unfortunately have not been consistently applied to chemical substances over time, particularly with respect to the patent literature.

Historically, chemical entities were often referred to by "common names" and/or by inconsistently applied IUPAC rules. Often, terms that were acceptable in earlier years (for example 'potash') later gave way to other standards (potassium carbonate). Little or no effort has been made to "normalize" the chemical nomenclature of the intellectual property (IP) databases retroactively over the decades.

Figure 1:
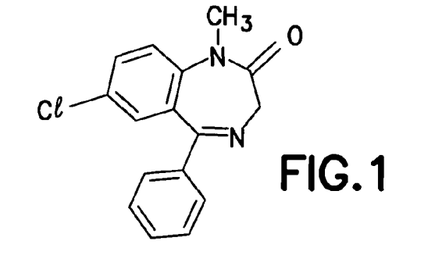
FIG. 1 shows the chemical structure of VALIUM®.

The problem of inconsistent naming is exemplified by considering the chemical names that have been applied to the drug VALIUM® (Valium is a registered trademark of Roche Products Inc.), the chemical structure of which is shown in FIG. 1. A list of some of the correct and incorrect names for VALIUM® that are found in the chemical and patent literature are shown in Table 1.

Table 1—Some of the Chemical Names Used for Valium® in Different Databases 7-chloro-1-methyl-5-phenyl-2H-1,4-benzodiazepin-2-one
7-chloro-1-methyl-5-phenyl-3H-1,4-benzodiazepin-2(1H)-one
7-chloro-1-methyl-5-phenyl-1,3-dihydro-2H-1,4-benzodiazepin-2-one
7-chloro-1-methyl-2-oxo-5-phenyl-3H-1,4-benzodiazepine
1-methyl-5-phenyl-7-chloro-1,3-diydro-2H-1,4-benzodiazepin-2-one
7-chloro-1,4-dihydro-1-methyl-5-phenyl-2H-1,4-benzodiazepin-2-one
7-chloro-1-methyl-5-3H-1,4-benzodiazepin-2(1H)-one Additionally, in the case of pharmaceuticals, the names of compounds of interest often change over time as compounds become commercialized. This has led to the frequent use of trade names or generic names in the scientific literature or in medical databases, which are not reflected retrospectively in the various IP databases. This has made it difficult to perform text searching for certain pharmaceuticals in the patent literature using commonly accepted phrases or definitions. For example, one cannot simply type in the search term "aspirin" or "VALIUM®" into any of the IP databases and find the pertinent patents for those chemical substances. The problem is further exacerbated by the fact that different brand names are often used in different countries to address language considerations of the different geographical areas. In fact, there are as many as 149 different names that have been employed in the literature for the drug VALIUM®, a number of which are illustrated in Table 2.

Table 2 - Some of the trade names used to refer to VALIUM®

ALBORAL, ALISEUM, ALUPRAM, AMIPROL, ANSIOLIN, ANSIOLISINA, APAURIN, APOZEPAM, ASSIVAL, ATENSINE, ATILEN, BIALZEPAM, CALMOCITENE, CALMPOSE, CERCINE, CEREGULART, CONDITION, DAP, DIACEPAN, DIAPAM, DIAZEMULS, DIAZEPAM, DIAZETARD, DIENPAX, DIPAM, DIPEZONA, DOMALIUM, DUKSEN, DUXEN, E-PAM, ERIDAN, EVACALM, FAUSTAN, FREUDAL, FRUSTAN, GIHITAN, HORIZON, KIATRIUM, LA-III, LEMBROL, LEVIUM, LIBERETAS, METHYL DIAZEPINONE, MOROSAN, NEUROLYTRIL, NOAN, NSC-77518, PACITRAN, PARANTEN, PAXATE, PAXEL, PLIDAN, QUETINIL, QUIATRIL, QUIEVITA, RELAMINAL, RELANIUM, RELAX, RENBORIN, RO 5-2807, S.A.R.L., SAROMET, SEDAPAM, SEDIPAM, SEDUKSEN, SEDUXEN, SERENACK, SERENAMIN, SERENZIN, SETONIL, SIBAZON, SONACON, STESOLID, STESOLIN, TENSOPAM, TRANIMUL, TRANQDYN, TRANQUASE, TRANQUIRIT, TRANQUO-TABLINEN, UMBRIUM, UNISEDIL, USEMPAX AP, VALEO, VALITRAN, VALRELEASE, VATRAN, VELIUM, VFVAL, VIVOL, WY-3467

Additionally, many chemical and drug patents make use of Markush structure references. These structures are generalized references to chemical structures where some substituent groups are specified in general terms, and a list of possible substitutents is enumerated. Thus, rather than a specific chemical compound being named, the Markush convention allows claimants to describe an entire series of compounds even if they have not specifically be synthesized or tested.

Figure 2A:
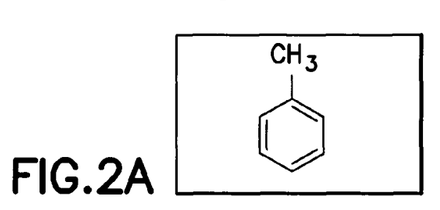
FIG. 2A illustrates the chemical composition of toluene, and where
Figure 2B:
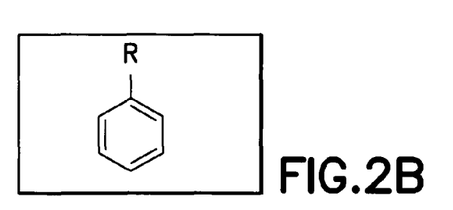
FIG. 2B illustrates a Markush representation that includes toluene.

For example, and referring to FIG. 2, rather than representing toluene (methylbenzene) as $C_6H_5$—$CH_3$, the Markush formulation allows one to represent an entire series of substituted benzenes as $C_6H_5$—R, where R is, by convention, any of a large number of carbon chains of various sizes. This convention further increases the difficulty of locating a chemical compound by normal searching techniques.

In U.S. Pat. No.: 6,304,869, Moore et al. describe a system to assign sub-structures to fragments given a complete structure connectivity description of a molecule, as well as a relational database system for storing this information. However, there is no concept of finding structures or substructures from names.

SUMMARY OF THE PREFERRED EMBODIMENTS

The foregoing and other problems are overcome, and other advantages are realized, in accordance with the presently preferred embodiments of these teachings.

This invention provides a system and a method to identify organic chemical nomenclature from text documents, and from that information to index chemical fragments and their structures and connectivity. This process can involve the grouping of multi-word entities into a single logical entity, and then the parsing of that entity into names of substructures. The text documents can be either well edited (where the rules for denoting such entities are followed) or ill formed. The system and method in accordance with this invention may be applied to both types of documents. Furthermore, only relatively small dictionaries need to be used.

Disclosed is a method, a computer program product and a system for processing documents that contain chemical names. In a system embodiment the system can include one computer, or a plurality of computers at least two of which are coupled together through a data communications network. The system has a unit to parse document text to recognize chemical name fragments; a unit to recognize any substructures present in the chemical name fragments; and a unit to determine structural connectivity information of the chemical name fragments and recognized substructures and to store the determined structural connectivity information in a searchable index.

The determined structural connectivity information is preferably stored in a searchable structure index, and the system further includes a unit to store text associated with processed documents in a text index, and a unit to search the text index using at least one of a fragment name and a substructure name and to search the structure index by at least one of fragment connectivity and substructure connectivity. At an intersection of the search results from the structure index and the text index, the system operates to identify at least one document that contains a reference to a corresponding chemical compound.

The unit that determines structural connectivity information looks up recognized fragments and substructures in a structure dictionary. In the preferred embodiment the structure dictionary is at least one of a MOL dictionary and a SMILES dictionary.

BRIEF DESCRIPTION OF THE DRAWINGS

The foregoing and other aspects of these teachings are made more evident in the following Detailed Description of the Preferred Embodiments, when read in conjunction with the attached Drawing Figures, wherein:

FIG. 2 illustrates a conventional Markush formulation, where

DETAILED DESCRIPTION OF THE PREFERRED EMBODIMENTS

By way of introduction, this invention uses a series of regular expressions, rules, and two small dictionaries to recognize chemical name fragments and combine them into organic chemical names. The use of the system and method of this invention is valuable in assisting parsers in recognizing multi-word chemical names that might otherwise be recognized as small fragments separated by punctuation that is part of the chemical names. Then, each chemical name is decomposed into fragments and indexed for text searching. If the fragment is known from a dictionary of known chemical structure fragments, the connectivity of this substructure is saved for indexing as well.

In more detail, it may be first assumed that the algorithm described in the above-referenced commonly assigned U.S. patent application Ser. No. 10/670,675 has identified as a chemical compound the string:

7-chloro-1-methyl-5-phenyl-3-dihydro-2H-1,4-benzodiazepin-2-one

The system and method in accordance with this invention then parses the above-given string into component fragment names, and indexes each of them separately. In this elementary example, the system and method finds the fragments between the hyphens: i.e., chloro; methyl; phenyl; 2H; dihydro; benzodiazepin; one; and produces a candidate list.

Figure 3:
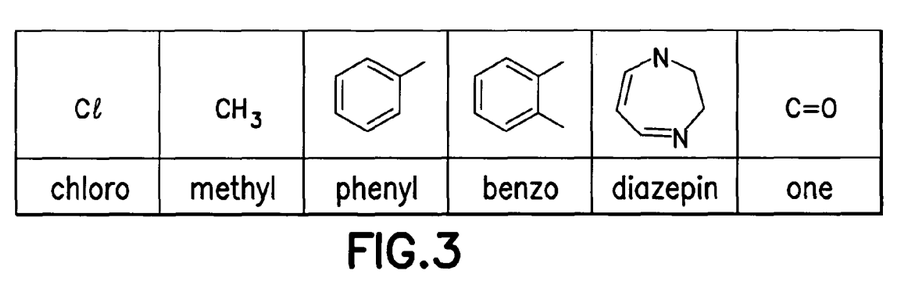
FIG. 3 shows various chemical substructures parsed from the chemical name for VALIUM®.

The candidate list is filtered in several steps, using several pattern rules and a small dictionary of known chemical substructures, resulting in the following list: chloro; methyl; phenyl; benzo; diazepin; one. Note that in this context the "one" fragment is not a number, but refers to a ketone substructure. The structures corresponding to these extracted fragment names are shown in FIG. 3.

As a result, the system and method are thus enabled to associate these name fragments with a dictionary of chemical structure fragments (CSFs) in an efficient manner. In addition, the dictionary of CSFs can contain graphical descriptions and be used provide a visual display to enhance the overall search process for compounds containing those entities.

Conversion of the chemical name fragments (CNFs) to CSFs implies that irrespective of the name a particular researcher or searcher uses, the user can search for any of these fragments by structure without having to select or specify the actual name used in the document.

Thus, while the numerous variations in the name of VALIUM® in Tables 1 and 2 are too extensive for a text search to be helpful, a search for the fragments by structure is much more likely to be successful.

In mining information from text documents, such as patents and technical articles, it is critical that long multi-word organic chemical nomenclatures be recognized properly so they can be grouped as single logical entities and correctly indexed. In the above-referenced commonly assigned U.S. patent application Ser. No. 10/670,675 the inventors Coden and Cooper previously described a system and method for grouping such nomenclature into logical entities without the need to provide large chemical dictionaries. This invention makes use of a search engine, such as one known as a JURUXML® search engine available from the assignee of this patent application, and a table of substructure names and connectivity. Such a table could, for example, be stored in a relational database such as one known as DB2™, also available from the assignee of this patent application.

Organic chemical names can be long, complex and may consist of several words separated by spaces. Organic chemical names should be recognized as a single noun phrase in order for the parsing of sentences in technical documents to proceed effectively. For example, terms such as chloroacetic acid, 4-allyl-2,6-dimethylphenol, 5-aminoalkyl-pyrazolo[4,3-D]-pyrimidine and 4-nitrobenzyl chloroformate each present specific term recognition challenges that previously could only be resolved by reference to a multi-million word chemical dictionary.

Further, while there are specific chemical rules for the spelling, spacing and punctuation of such chemical entities, they are not always rigorously followed, especially in the patent literature. Examples abound of chemical names broken up by incorrect spaces or hyphens which must be recombined for the overall term to be recognized successfully.

There are several common methods of representing the connectivity of organic chemical structures. Two such formats are referred to as MOL files and SMILES files. MOL files (from Molecular Design Ltd) contain the coordinates of each atom along with a connectivity matrix, while SMILES files represent connectivity using letters for each atom and symbols for the various bonds, see "SMILES 1. Introduction and Encoding Rules", Weininger, D., *J.Chem. Inf: Comput. Sci.* 1988, 28,31. Both the MOL and SMILES approaches can be used to represent extremely complex structures. This invention assumes that a table of such connectivity representations is available for the common molecular fragments that can be named in chemical structures, such as methyl, phenyl and so forth, in at least one of these common formats, or that a parser exists to read data in these formats and convert it into an internal structural representation. Such parsers are well known in the art and are readily available.

This invention generally has two phases or aspects: a first relates to the indexing of chemical structural fragments, and a second relates to returning query results of such fragments. In the indexing phase of the invention it is assumed that a series of chemically-related documents, such as chemical or drug patents or articles, are scanned and indexed.

Indexing Patents and Articles

In the indexing phase, each document is analyzed and the text indexed by a search engine. Then, organic chemical names are identified and the fragment names in these names are also added to the index. Finally, for each fragment that the analysis system finds within each organic chemical name, it looks up that name in a substructure dictionary. If that substructure is found in the dictionary, it is added to a structure index for that document.

Each chemical name is broken into fragments using a tokenizer that separates tokens based on any of the punctuation characters—( )[ ]#'0123456789 and space. Then, those fragments are eliminated that contain numbers.

For example, for the chemical name:

7-chloro-1-methyl-5-phenyl-3-dihydro-2H-1,4-benzodiazepin-2-one that was mentioned above, the parser extracts the substructure fragments: chloro; methyl; phenyl; dihydro; benzodiazepin; one. Next a substructure string search is applied to these fragments, breaking them down further: chloro; methyl; phenyl; dihydro; benzo; diazepin; one. These strings are then looked up in a structure dictionary, and for those that are found, a substructure entry is made. The corresponding SMILES strings are as follows:

Cl
[CH3]
c1ccccc1
c1ccccc1
c1ncccncc1
C=O.

Figure 4:
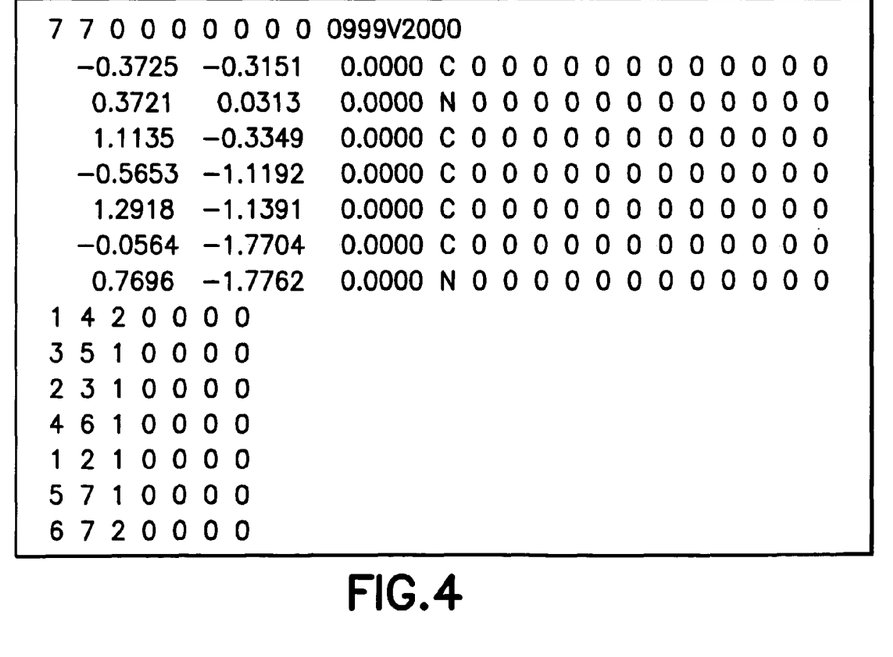
FIG. 4 shows a MOL file representation of a diazepin fragment.

An analogous set of entries can also be made for the MOL file representations, which represent atomic coordinates and connectivity numerically. For example, the MOL file representation of the diazepin fragment is shown in FIG. 4.

It should be noted that this approach goes well beyond just synonym expansion, as the method expands molecule names to their substructures and represents these substructures so that they can be searched for without reference to the name used in that particular molecular name.

Searching the Indexes

In the search phase, the user enters search terms and structures. For example, to enter a SMILES format substructure query, the user would enter "c1ccccc1" for a phenyl group and "C=O" for a carbonyl group, along with one or more search terms such as "antidepressant" or "antibiotic" (or whatever other term(s) that may have been saved in the text index 715 shown in FIG. 7, such as author name, article title or, for the case of a patent document, the patent number, the assignee name, etc.) The results of the structure search and the text search are combined and their intersection is returned to the user.

In commonly assigned U.S. patent application Ser. No. 10/670,675 there is described a system and a method for recognizing chemical names algorithmically, without resort to large compendia of chemical knowledge. Described herein is a system and, method for indexing chemical names into chemical fragments which can be correlated with chemical connectivity tables.

The method includes recognizing the chemical name, and finding its fragmentary components. The fragments are indexed for insertion into chemical connectivity tables (such as in MOL and/or SMILES representation) and possibly also for text search, and those fragments whose substructures are known are indexed into chemical connectivity tables as well. Furthermore, the method handles those chemical fragments that were written not following the standard rules of writing such entities, or that contain erroneous spaces and/or characters caused by, for instance, the use of OCR software.

Recognizing Organic Chemical Fragments

Algorithms used for indexing organic chemical names are now described. The use of the system and method results in both a text-based search index by chemical fragment name and a substructure search based on chemical structure connectivity.

A. It is assumed that each document to be indexed is parsed using text analytics and organic chemical name recognition. A presently preferred technique for performing this function is described in the commonly assigned U.S. patent application Ser. No. 10/670,675, however the use of this invention is not limited only to the use of only the technique described in commonly assigned U.S. patent application Ser. No. 10/670,675.

B. Each organic chemical name is broken into chemical subtokens wherever parts of the longer name are separated by specific tokens. In this preferred embodiment, these tokens include, but need not be limited to, hyphens, parentheses, brackets and braces.

C. Each subtoken that does not contain a number is added to a search index.

D. Each subtoken that does not contain a number is looked up in a chemical fragment dictionary and its connectivity information retrieved, if it exists. This connectivity information is added to a chemical substructure index (shown in FIG. 7 as the structure index 719).

Figure 7:
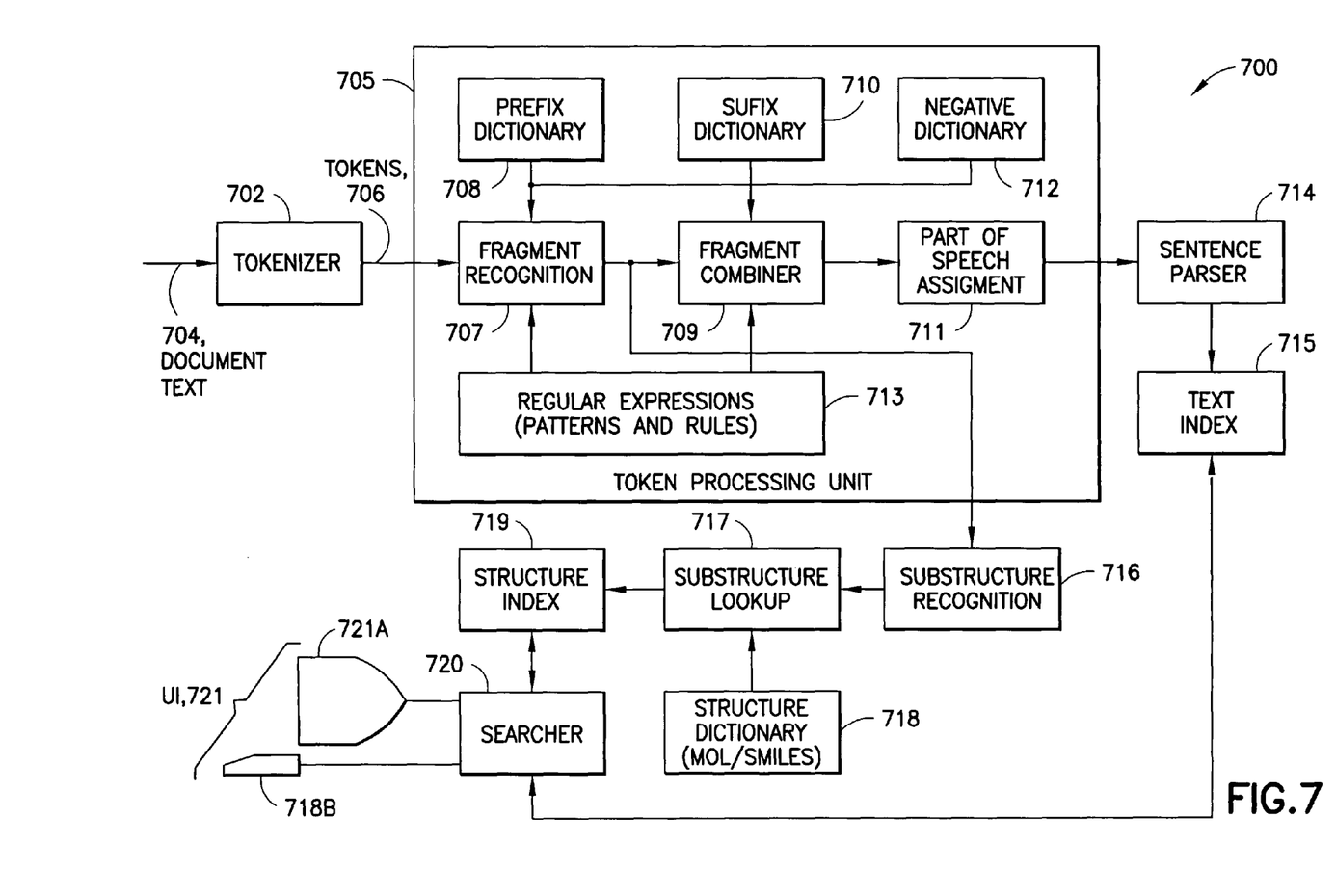
FIG. 7 is a block diagram of an exemplary embodiment of a computer system that is suitable for practicing the method of this invention.

E. The chemical substructure index 719 maybe, as non-limiting examples, a text file, an XML file, or a relational database. Each substructure may represent connectivity in either the MOL file or SMILES representation.

F. The user of a search system enters one or more fragment names and selects one or more substructures, either by name or by graphical representation (such as by using a pointing device to select a particular graphical representation of a chemical structure from a pull-down or pop-up menu of possible choices).

G. The search system returns the identification of documents, and possibly copies of the documents themselves, where chemical compounds have been found that contain the selected substructure names and the connectivity specified by the selected substructures and/or fragments.

Figure 5:
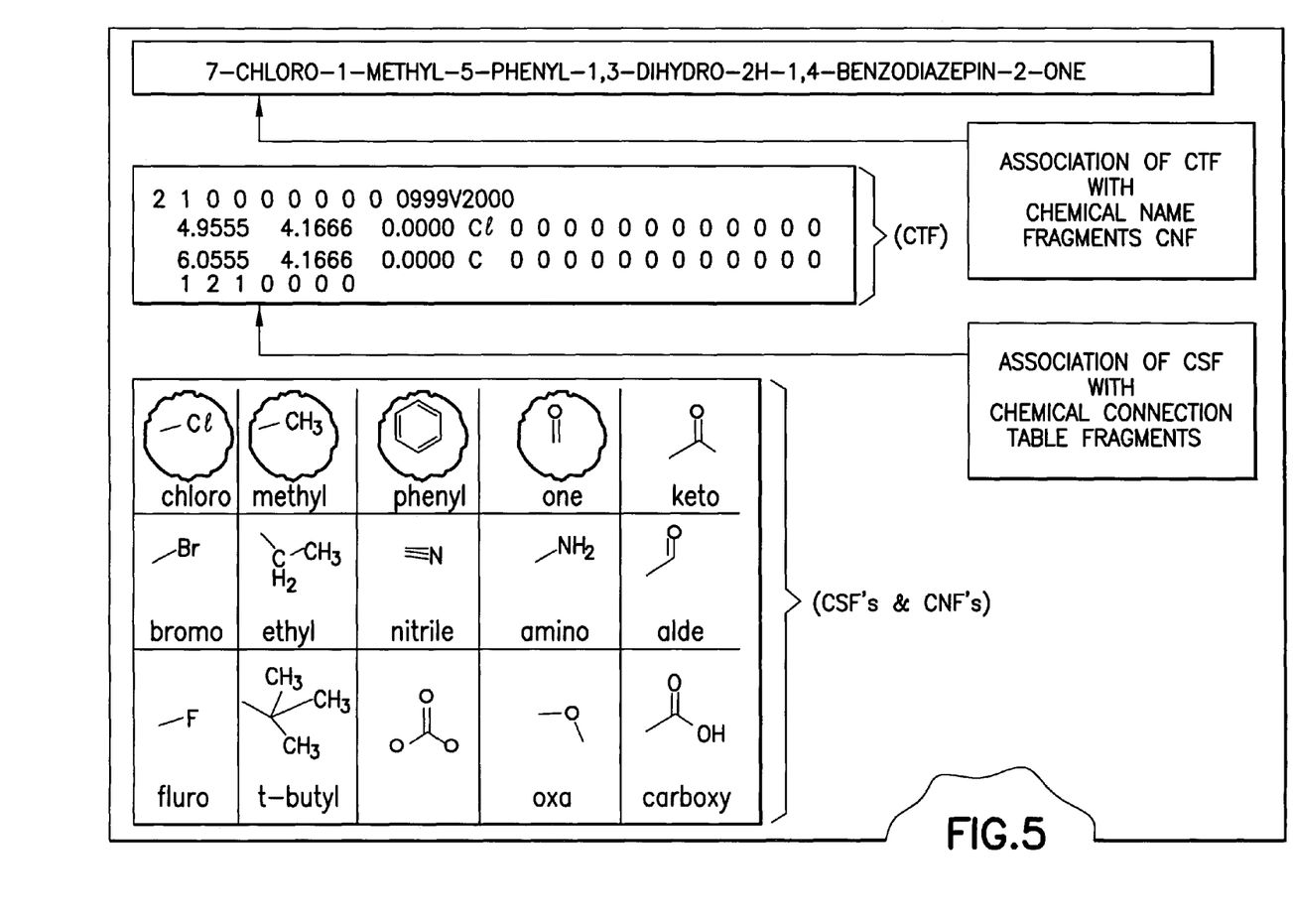
FIG. 5 illustrates correlating chemical structure fragments with connectivity tables.

FIG. 5 shows the general process of correlating chemical structure fragments with connectivity tables, where CTF represents chemical connection table fragments. The CNF represents chemical name fragment and the CSF is the chemical structure fragment, as defined above.

Figure 6A:
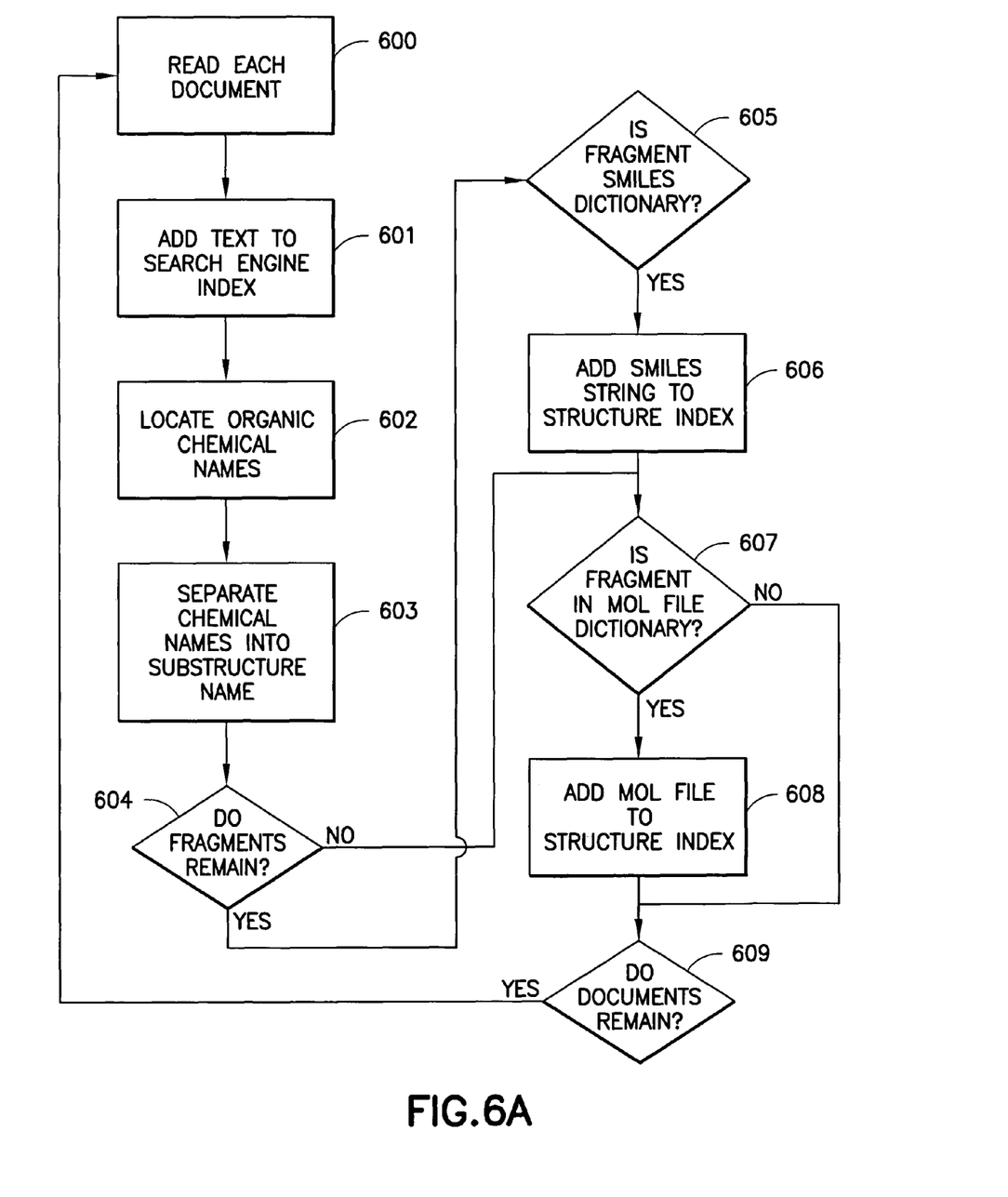
FIG. 6A is a logic flow diagram that illustrates the overall flow of an indexing algorithm in accordance with this invention.

FIG. 6A describes indexing a collection of documents. Each document is read in from a file (block 600) and indexed (block 601) in a conventional manner using a search engine, such as the JURUXML® search engine. In the presently preferred embodiment the algorithm described in the commonly assigned U.S. patent application Ser. No. 10/670,675 is then used to identify organic chemical names (block 602). Each organic chemical name is separated into sub-tokens, separated by, for example, hyphens, spaces and parenthesis (block 603).

In a loop, the system and method tests to see if more fragment tokens remain (block 604). If they do remain, the next fragment token is obtained and tested to see if it occurs in a dictionary of SMILES fragments (block 605). If it does, the SMILES expression is added to the structure index (block 606). Then, a test is preferably also made to determine if the fragment occurs in the MOL file dictionary (block 607). If it does, it is added to the structure index as well (block 608). A test is then made to determine if there are more documents to be processed (block 609). If there are, control passes to block 600 to continue processing the remaining documents, and if not the indexing operation is completed. The processing of fragments implies as well the processing of substructures that may make up a certain fragment.

Figure 6B:
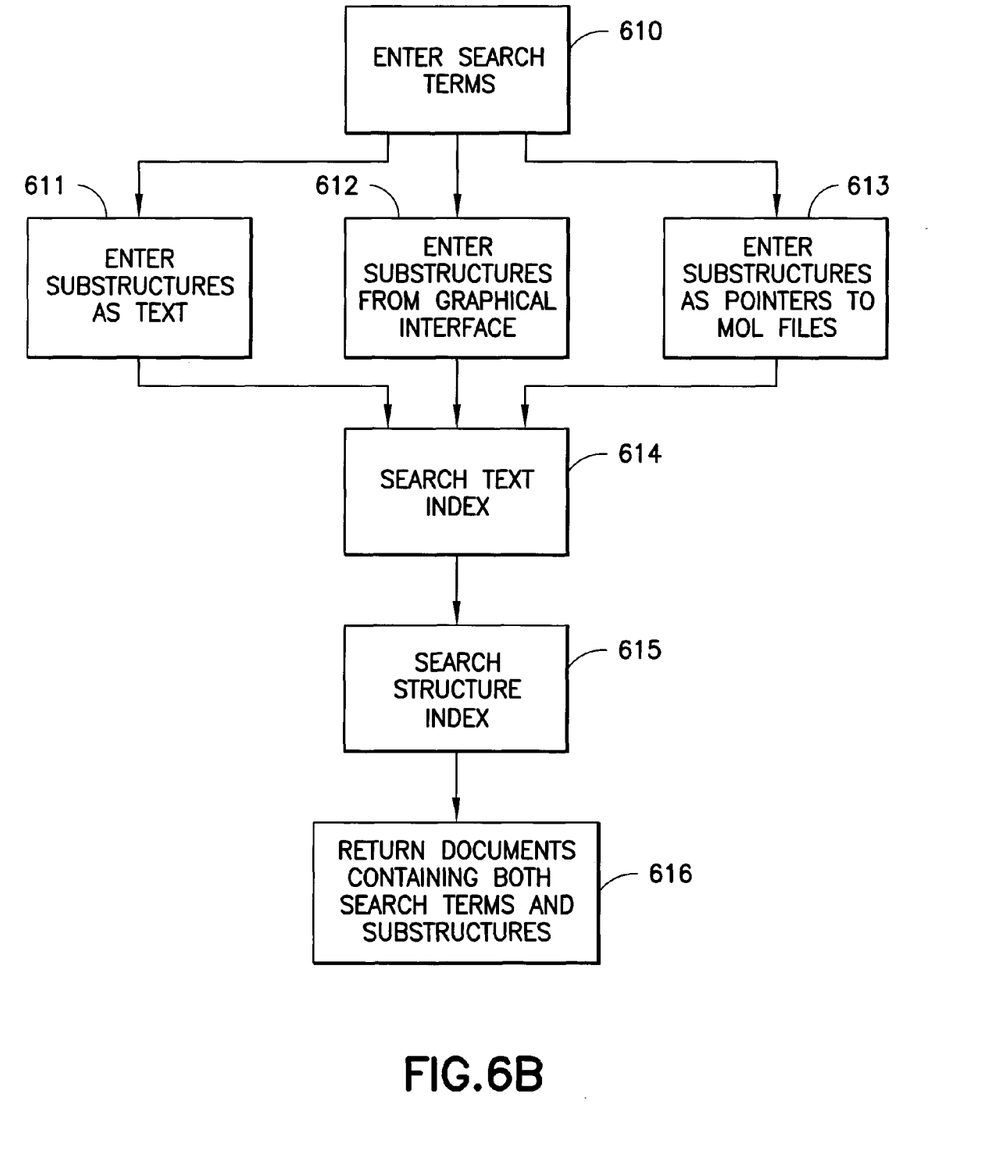
FIG. 6B illustrates the logic flow of a presently preferred search algorithm.

FIG. 6B describes how a user performs a search against the system. The user first enter search terms (block 610), and then optionally the user enters substructures either as text, such as SMILES text (block 611), or using a graphical user interface (GUI) as a pointer to a graphical list of structures (block 612), or the user enters a pointer to a MOL file (block 613). The system then searches the text index (block 614) and the structure index (block 615), and what is returned is the intersection of the results (block 616). The results identify one or more documents where there are found chemical compounds that contain the desired substructures and the specified search terms.

FIG. 7 is a block diagram of a document processing system 700 that incorporates functional blocks (702-714) of the commonly assigned U.S. patent application Ser. No. 10/670,675, and that further incorporates functional blocks (715-721) in accordance with this invention. As such, it is assumed that the system 700 contains a standard tokenizer 702 for separating input document text 704 into tokens 706 based on blank spaces. The tokens 706 are examined where they match a set of defined patterns. Furthermore the tokens 706 are examined in the context of the adjacent tokens, to determine whether the tokens 706 are part of a chemical fragment. More specifically, the system 700 includes a token processing unit 705 for determining semantic meaning of words, such as by assigning corresponding associated parts of speech to words found in the document. The token processing unit 705 may be constructed to include sub-units 707, 709 and 711 for applying a plurality of regular expressions and rules, and a plurality of dictionaries, to recognize organic chemical name fragments (sub-unit 707), for combining recognized organic chemical name fragments into a complete organic chemical name (sub-unit 709), and for assigning the complete organic chemical name with one part of speech, preferably a noun (sub-unit 711). The aforementioned dictionaries of the system 700 can include a prefix dictionary 708 (containing a list of common prefixes for the technical terms of interest), a suffix dictionary 710 (containing a list of common suffixes for the technical terms of interest), and an optional negative dictionary 712. The negative dictionary 712, if used, contains words that may occur within the input document text 704, but that do not form a meaningful part of a technical term (e.g., do not form a part of an organic chemical compound). Basically, the negative dictionary 712 includes a list of words that can be ignored. Examples of words that may be found in the negative dictionary 712 are "saline" and "formula". It should be appreciated that the contents of the dictionaries 708, 710 and 712 can change and evolve over time, and over the use of the system 700, either manually or automatically. The plurality of regular expressions (patterns) and rules can be stored in a database 713, and may also change and evolve over time, and over the use of the system 700, either manually or automatically. The output of the token processing unit 705 can form an input to a further unit 714 that parses sentences into their component parts based at least in part on the determined semantic content, such as assigned parts of speech (including the noun part of speech assigned to recognized organic chemical names).

In the operation of the token processing unit 705 the application of regular expressions and rules results in punctuation characters being one of maintained or removed between chemical name fragments as a function of context. The regular expressions can include a plurality of patterns, where individual patterns can be at least one of characters, numbers and punctuation. For example, the punctuation can include at least one of parenthesis, square bracket, hyphen, colon and semi-colon, and the characters can include at least one of upper case C, O, R, N and H, as well as strings of at least one of lower case xy, ene, ine, yl, ane and oic.

The output of the sentence parser 714 is applied to a text index 715, where for each examined document there is a list of associated text found in that document. Examples of text can include author(s) names and keywords such as "antidepressant", "antiseptic", "protein", etc., as well as the recognized names of chemical compounds.

In addition, the output of the fragment recognition block 707 is applied to a substructure recognition block 716. Using again the example given above of the organic chemical name:

7-chloro-1-methyl-5-phenyl-3-dihydro-2H-1,4-benzodiazepin-2-one, the fragment recognition block 707 extracts the substructure fragments: chloro; methyl; phenyl; dihydro; benzodiazepin; one. These fragments are then applied to the substructure recognition block 716, where the substructure string search is applied to these fragments, breaking them down further where possible into the substructures: chloro; methyl; phenyl; dihydro; benzo; diazepin; one. These substructure strings (some being the original fragments, and some possibly being substructures that make up one or more of the fragments) are then input to a substructure lookup block 717 where, in cooperation with at least one structure dictionary 718 (e.g., one or both of a MOL or SMILES dictionary), the substructure strings are looked up in the structure dictionary 718, and for those that are found, a substructure entry is made in a structure index 719.

Coupled with the structure index 719 and with the text index 715 is a searcher 720 and a user interface (UI) 721, such as a graphical user interface (GUI) comprised of a display 721A and a keyboard 721B. By means of the UI 721 and searcher 720 the user is enabled to perform the search method disclosed above in association with FIG. 6B.

The foregoing description has provided by way of exemplary and non-limiting examples a full and informative description of the best method and apparatus presently contemplated by the inventors for carrying out the invention. However, various modifications and adaptations may become apparent to those skilled in the relevant arts in view of the foregoing description, when read in conjunction with the accompanying drawings and the appended claims. For example, only one of the MOL or SMILES chemical representation systems may be used, or another type of representation system may be employed alone or in combination with one or both of the MOL and SMILES systems. However, all such and similar modifications of the teachings of this invention will still fall within the scope of this invention.

It should be further appreciated that the system 700 could be implemented in a network environment, and that components of the system 700 maybe distributed across multiple computers. The network environment may contain two or more computers connected by a local or a wide area network, (e.g., Ethernet, Token Ring, the telephone network, and the Internet), and a user may access a hypermedia or other object database using a client application on the user's computer. The client application may communicate with a search server (e.g., a hypermedia object database search system) located on a client computer or another computer (e.g., one or more servers) on the network. To process queries from users, the search server may access a database index, which may be located on the same computer as the search server or on another computer on the network. The document objects in a database may be located on any computer on the network. In this invention certain of the functional units and modules shown in FIG. 7; such as the token processing unit 705 and components of the token processing unit 705, as well as the substructure recognition 716, substructure lookup, structure dictionary 718 and structure index 719 (as well as the text index 715) may be located on two or more computers, and may be coupled together by one or more data communications networks. One or more of the connections between the tokenizer 702 and the token processing unit 705, and/or the token processing unit 705 and the sentence parser 714, and/or the fragment recognition unit 707 and the substructure recognition unit 716, may also be implemented over data communications networks, including local and wide area networks, such as the Internet. The input to the tokenizer 702 and the output from the sentence parser 714 may also be implemented using one or more networks. The user may query the system 700 over a network, such as the Internet, and the system 700 may form a part of a network-based, e.g., a Web-based, service such as, by example only, a data mining type of service.

Further, while the method and apparatus described herein are provided with a certain degree of specificity, the present invention could be implemented with either greater or lesser specificity, depending on the needs of the user.

Further still, some of the features of the present invention could be used to advantage without the corresponding use of other features. As such, the foregoing description should be considered as merely illustrative of the principles of the present invention, and not in limitation thereof.

What is claimed is:

1. A method to process at least one text document, comprising:
    partitioning text of each of the at least one text document into text tokens;
    assigning semantic meaning to words of the partitioned text token, where assigning comprises applying a plurality of regular expressions, rules and a set of dictionaries,
    where the set of dictionaries is selected from the group consisting of:
    a first collection of dictionaries consisting of a common chemical prefix dictionary and a common chemical suffix dictionary to recognize chemical name fragments and
    a second collection of dictionaries consisting of the common chemical prefix dictionary, the common chemical suffix dictionary to recognize chemical name fragments and a dictionary of stop words to eliminate erroneous chemical name fragments;
    recognizing any substructures present in the chemical name fragments;
    extracting keywords from the text document, where the keywords are associated with the recognized chemical name fragments and the substructures;
    indexing the extracted keywords in a text index;
    adding each of the recognized chemical name fragments and the substructures that do not contain a number to the text index;
    determining structural connectivity information within each of the recognized chemical name fragments and the substructures that do not contain a number;
    indexing representations of the recognized chemical name fragments and the substructures in association with the determined structural connectivity information into a plurality of chemical connectivity tables of a chemical substructure index, where indexing the representations comprises, for each of the at least one text document:
        in a loop, testing each of the recognized chemical name fragments in the at least one text document to see if the recognized chemical name fragment occurs in a dictionary of SMILES fragments, where if it does then a SMILES expression for the recognized chemical name fragment is added to the chemical substructure index,
        then determining if the recognized chemical name fragment occurs in a MOL file dictionary, where if it does then a MOL file expression for the fragment token is added to the chemical substructure index, and
        storing the text index in association with the chemical substructure index;
    providing a graphical user interface to search the text index and the chemical substructure index, where the graphical user interface comprises a graphical list of substructures
    where the search comprises first entering search terms comprising one or more chemical fragment names and then selecting graphical representations of one or more substructures, where the selecting comprises using the graphical user interface as a pointer to the graphical list of substructures; and
    receiving a search result, where the search result is an intersection of the chemical substructure index and the text index, identifying at least one text document where there are found chemical compounds that contain the selected substructures, and connectivity specified by the one or more chemical fragment names and the selected substructures and where the search terms are found in the text index.

2. The method as in claim 1, wherein the search further comprises first entering search terms comprising the one or more chemical fragment names and entering at least one keyword, and where the search result is identifying at least one text document where there are found the at least one keyword, the chemical compounds that contain the selected substructures, and the connectivity specified by the one or more chemical fragment names and the selected substructures.

3. A method as in claim 1 performed by executing a computer program product.

4. The method as in claim 1, where determining structural connectivity information comprises looking up recognized chemical name fragments and substructures in a structure dictionary.

5. The method as in claim 1, further comprising filtering recognized chemical name fragments using a list of stop words to eliminate erroneous chemical name fragments.

6. The method as in claim 1, where chemical name fragments are further recognized by using common chemical word endings.

7. The method as in claim 1, where application of said regular expressions and rules results in punctuation characters being one of maintained or removed from between chemical name fragments as a function of context.

8. The method as in claim 1, where said regular expressions comprise a plurality of patterns, individual ones of which are comprised of at least one of characters, numbers and punctuation.

9. The method as in claim 8, where the punctuation comprises at least one of a parenthesis, a square bracket, a hyphen, a colon and a semi colon.

10. The method as in claim 8, where the characters comprise upper case C, O, R, N and H.

11. The method as in claim 8, where the characters comprise lower case xy, ene, ine, yl, ane and oic.

12. The method as in claim 1, comprising an initial step of tokenizing the text document to provide a sequence of tokens.

13. A system having at least one computer, comprising:
    a tokenizer module and a token processing module comprised of computer instructions in data storage distributed across the at least one computer directing the at least one computer to partition text of each of at least one text document into text tokens and to assign semantic meaning to words of the partitioned text token by applying a plurality of regular expressions, rules and a set of dictionaries,
    where the set of dictionaries is selected from the group consisting of:
    a first collection of dictionaries consisting of a common chemical prefix dictionary and a common chemical suffix dictionary to recognize chemical name fragments and
    a second collection of dictionaries consisting of the common chemical prefix dictionary, the common chemical suffix dictionary to recognize chemical name fragments and a dictionary of stop words to eliminate erroneous chemical name fragments;
    the instructions of the token processing module directing the at least one computer to recognize any substructures present in the chemical name fragments;
    the instructions of the token processing module directing the at least one computer to extract keywords from the text document, where the keywords are associated with the recognized chemical name fragments and the substructures and to index the extracted keywords in a text index;

the instructions of the token processing module directing the at least one computer to add each of the recognized chemical name fragments and the substructures that do not contain a number to the text index;

the instructions of the token processing module directing the at least one computer to, for each of the at least one text document, determine structural connectivity information within each of the recognized chemical name fragments and the substructures that do not contain a number, and to index representations of the recognized chemical name fragments and the substructures in association with the determined structural connectivity information into a plurality of chemical connectivity tables of a chemical substructure index, where indexing the representations comprises:

in a loop, testing each of the recognized chemical name fragments in the at least one text document to see if the recognized chemical name fragment occurs in a dictionary of SMILES fragments, where if it does then a SMILES expression for the recognized chemical name fragment is added to the chemical substructure index, then determining if the recognized chemical name fragment occurs in a MOL file dictionary, where if it does then a MOL file expression for the fragment token is added to the chemical substructure index, and the instructions of the token processing module directing the at least one computer to store the text index in association with the chemical substructure index;

a searcher module comprised of computer instructions distributed across the at least one computer and a graphical user interface comprised of a display configured to display a graphical list of substructures and a keyboard connected to a computer of the at least one computer directing the at least one computer to search the text index and the chemical substructure index, where the search comprises first entering one or more chemical fragment names and then selecting graphical representations of one or more substructures, where the selecting comprises using the graphical user interface as a pointer to the graphical list of substructures; and the graphical user interface configured to receive a search result, where the search result is an intersection of the chemical substructure index and the text index, identifying at least one text document where there are found chemical compounds that contain the selected substructures, and connectivity specified by the one or more chemical fragment names and the selected substructures and where the search terms are found in the text index.

14. The system as in claim 13, wherein the search further comprises first entering the one or more chemical fragment names and additionally entering at least one keyword, and where the search result is identifying at least one text document where there are found the at least one keyword, the chemical compounds that contain the selected substructures, and the connectivity specified by the one or more chemical fragment names and the selected substructures.

15. The system as in claim 13, where the instructions of said token processing module that directs the at least one computer to determine the structural connectivity information further directs the at least one computer to look up recognized fragments and substructures in a structure dictionary.

16. The system as in claim 13, further comprising the instructions of said token processing module further directs the at least one computer to filter recognized chemical name fragments using a list of stop words to eliminate erroneous chemical name fragments.

17. The system as in claim 13, where the instructions of the tokenizer module further directs the at least one computer to recognize chemical name fragments by using common chemical word endings.

18. The system as in claim 13, where application of said regular expressions and rules results in punctuation characters being one of maintained or removed from between chemical name fragments as a function of context.

19. The system as in claim 13, where said regular expressions comprise a plurality of patterns, individual ones of which are comprised of at least one of characters, numbers and punctuation.

20. The system as in claim 19, where the punctuation comprises at least one of a parenthesis, a square bracket, a hyphen, a colon and a semi colon.

21. The system as in claim 19, where the characters comprise upper case C, O, R, N and H.

22. The system as in claim 19, where the characters comprise lower case xy, ene, ine, yl, ane and oic.

23. The system as in claim 13, further comprising an input tokenizer module comprised of computer instructions directing the at least one computer to receive text documents to be processed to provide a sequence of tokens.

24. A system comprising a plurality of computers at least two of which are coupled together through a data communications network, said system comprising:

a tokenizer and a token processing module comprised of computer instructions in data storage distributed across the plurality of computers directing the plurality of computers to parse text of each of at least one text document into text tokens and assign semantic meaning to words of the parsed text tokens, where assigning comprises applying a plurality of regular expressions, rules and a set of dictionaries, where the set of dictionaries is selected from the group consisting of:

a first collection of dictionaries consisting of a common chemical prefix dictionary and a common chemical suffix dictionary to recognize chemical name fragments and a second collection of dictionaries consisting of the common chemical prefix dictionary, the common chemical suffix dictionary to recognize chemical name fragments and a dictionary of stop words to eliminate erroneous chemical name fragments;

the instructions of the token processing module directing the plurality of computers to recognize any substructures present in the chemical name fragments;

the instructions of the token processing module directing the plurality of computers to extract keywords from the text document, where the keywords are associated with the recognized chemical name fragments and the substructures and to index the extracted keywords in a text index;

the instructions of the token processing module directing the plurality of computers to add each of the recognized chemical name fragments and the substructures that do not contain a number to the text index;

the instructions of the token processing module directing the plurality of computers to, for each of the at least one text document, determine structural connectivity information within each of the recognized chemical name fragments and the substructures that do not contain a number;

the instructions of the token processing module directing the plurality of computers to index representations of the recognized chemical name fragments and the substructures in association with the determined structural connectivity information into a plurality of chemical connectivity tables of a chemical substructure index, where indexing the representations comprises:

in a loop, testing each of the recognized chemical name fragments in the at least one text document to see if the recognized chemical name fragment occurs in a dictionary of SMILES fragments, where if it does then a SMILES expression for the recognized chemical name fragment is added to the chemical substructure index, then determining if the recognized chemical name fragment occurs in a MOL file dictionary, where if it does then a MOL file expression for the fragment token is added to the chemical substructure index, and storing the text index in association with the chemical substructure index;

a searcher module comprised of computer instructions distributed across the plurality of computers and a graphical user interface comprised of a display configured to display a graphical list of substructures and a keyboard connected to a computer of the plurality of computers directing the plurality of computers to search the text index and the chemical substructure index, where the search comprises first entering search terms comprising one or more chemical fragment names and then selecting graphical representations of one or more substructures, where the selecting comprises using the graphical user interface as a pointer to the graphical list of substructures; and the graphical user interface configured to receive a search result, where the search result is an intersection of the chemical substructure index and the text index, identifying at least one text document where there are found chemical compounds that contain a reference to the search temis and the one or more substructures and where the search terms are found in the text index.

25. The system as in claim 24, wherein the search further comprises first entering the one or more chemical fragment names and additionally entering at least one keyword, and where the search result is identifying at least one text document where there are found the at least one keyword, the chemical compounds that contain the selected substructures, and the connectivity specified by the one or more chemical fragment names and the selected substructures.

26. The system as in claim 24, where the instructions of said token processing module further direct the plurality of computers to look up recognized fragments and substructures in a structure dictionary.

* * * * *